United States Patent
Atwell

(10) Patent No.: US 10,758,299 B2
(45) Date of Patent: Sep. 1, 2020

(54) ELECTRODE ASSEMBLY

(71) Applicant: Gyrus Medical Limited, Cardiff (GB)

(72) Inventor: Tony Atwell, Wales (GB)

(73) Assignee: Gyrus Medical Limited, Cardiff (GB)

( * ) Notice: Subject to any disclaimer, the term of this patent is extended or adjusted under 35 U.S.C. 154(b) by 752 days.

(21) Appl. No.: 15/497,834

(22) Filed: Apr. 26, 2017

(65) Prior Publication Data

US 2017/0333114 A1    Nov. 23, 2017

(30) Foreign Application Priority Data

May 23, 2016  (GB) .................................. 1609019.3

(51) Int. Cl.
*A61B 18/14* (2006.01)
*A61B 18/00* (2006.01)
*A61B 17/00* (2006.01)

(52) U.S. Cl.
CPC .... *A61B 18/1445* (2013.01); *A61B 17/00234* (2013.01); *A61B 2018/00184* (2013.01); *A61B 2018/00517* (2013.01); *A61B 2018/00601* (2013.01); *A61B 2018/141* (2013.01); *A61B 2018/144* (2013.01); *A61B 2018/1452* (2013.01)

(58) Field of Classification Search
CPC .......... A61B 17/00234; A61B 18/1445; A61B 2018/00184; A61B 2018/00517; A61B 2018/00601; A61B 2018/141; A61B 2018/144; A61B 2018/1452
See application file for complete search history.

(56) References Cited

U.S. PATENT DOCUMENTS

| | | | |
|---|---|---|---|
| 5,007,907 A | | 4/1991 | Nishigaki et al. |
| 5,437,665 A | * | 8/1995 | Munro ................... A61B 18/14 606/41 |
| 6,322,494 B1 | | 11/2001 | Bullivant et al. |
| 6,494,881 B1 | * | 12/2002 | Bales ................... A61B 18/149 606/41 |
| 2006/0229600 A1 | | 10/2006 | Canady |
| 2007/0282328 A1 | * | 12/2007 | Yahagi ............... A61B 18/1492 606/45 |
| 2012/0296332 A1 | | 11/2012 | Chernov et al. |

FOREIGN PATENT DOCUMENTS

| | | |
|---|---|---|
| EP | 1864622 A2 | 12/2007 |
| WO | WO-2006/036326 A2 | 4/2006 |

OTHER PUBLICATIONS

Maskery, D., "UK Search Report", prepared for application No. 1609019.3, dated Nov. 16, 2016, 3 pages.

* cited by examiner

*Primary Examiner* — Michael F Peffley
*Assistant Examiner* — Tigist S Demie
(74) *Attorney, Agent, or Firm* — Winstead PC

(57) ABSTRACT

An electrode assembly (3) is provided for use in a resectoscope, the electrode assembly (3) comprising a pair of arms (4), and a tissue treatment element (9) depending from the arms. The arms (4) are pivotably mounted one to the other such that they are movable between a retracted position in which they lie alongside one another and a deployed position in which they diverge one from another. The electrode assembly (3) includes actuation means for moving the arms between their retracted and deployed positions. The tissue treatment element (9) is disposed at the distal end of each arm such that it is movable between at least two different operating positions.

5 Claims, 3 Drawing Sheets

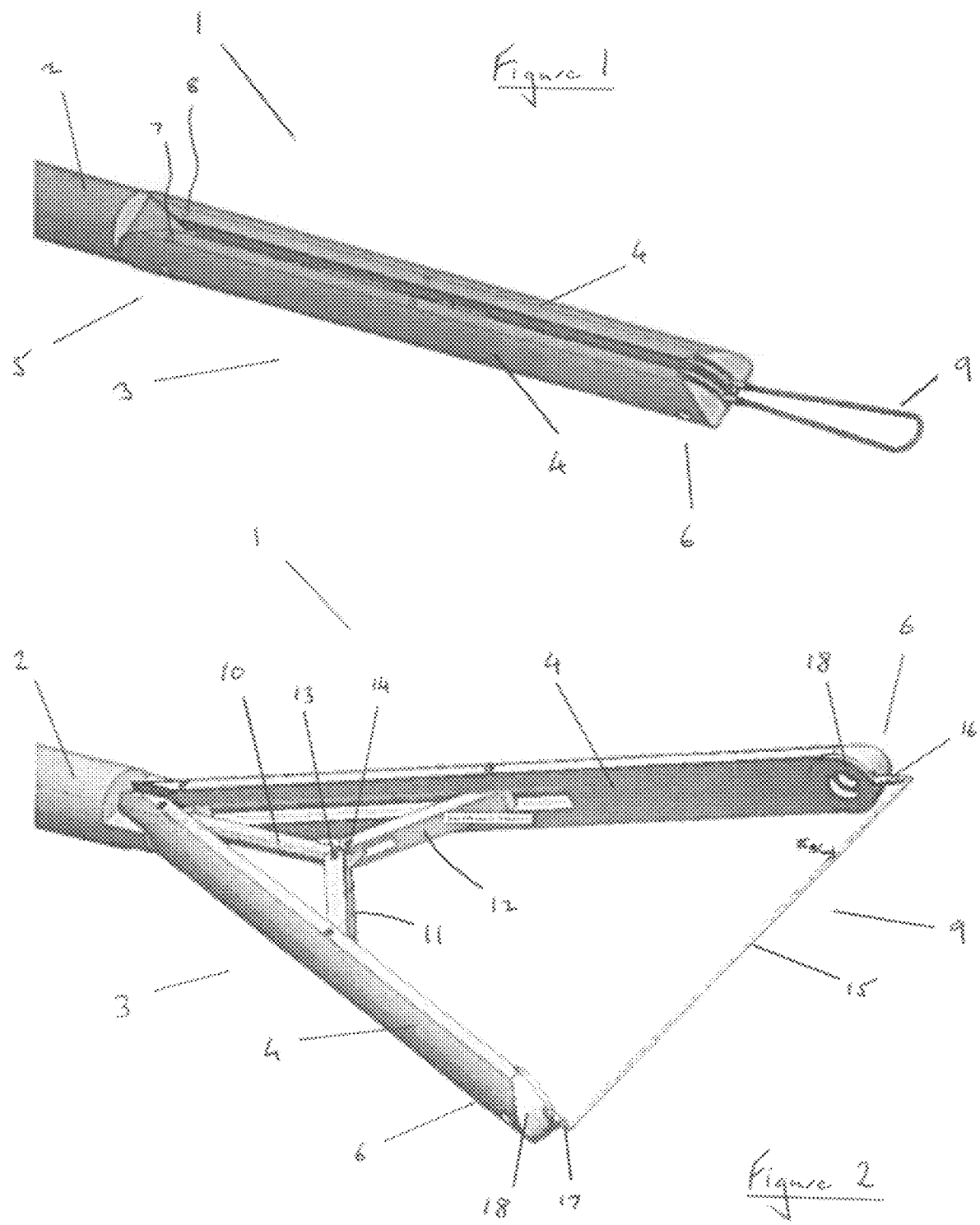

ELECTRODE ASSEMBLY

BACKGROUND OF THE INVENTION

This invention relates to an electrode assembly for a surgical instrument for the treatment of tissue, particularly an electrosurgical endoscopic instrument. Such systems are commonly used for the vaporisation and/or coagulation of tissue in surgical intervention, most commonly in "keyhole" or minimally invasive surgery.

One type of electrosurgical procedure is endoscopic urological surgery using a resectoscope. Such systems are well known in the art, examples being given in U.S. Pat. Nos. 5,007,907 and 6,322,494. Such systems include an electrosurgical instrument deployable by means of a resectoscope, and an electrosurgical generator powering the instrument. Instruments used in electrosurgical urology surgery are either bipolar, in which case two electrodes are present at the distal end of the instrument, or monopolar, in which case one electrode is present on the instrument and a second electrode is provided in the form of a patient return plate.

Bladder tumour resection is often difficult due to the curved shape of the tissue, and the fact that there is no clear dissection plane visible to the surgeon. Deviating from the ideal depth of tissue removal either means that insufficient tissue is removed, or the too much tissue is removed, including the possibility of perforating the bladder.

SUMMARY OF THE INVENTION

The present invention attempts to provide a solution to this problem by providing an electrode assembly for use in a resectoscope, the electrode assembly comprising a pair of arms, the arms being pivotably mounted one to the other such that they are movable between a retracted position in which they lie alongside one another and a deployed position in which they diverge one from another, arm actuation means for moving the arms between their retracted and deployed positions, a tissue treatment element depending from the arms, and connection means for connecting the tissue treatment element to a source of electrosurgical energy, characterised in that the tissue treatment element is disposed at the distal and of each arm such that it is movable between at least two different operating positions.

The above instrument can be inserted into a surgical site such as the bladder of a patient using a resectoscope with the arms in their retracted position such that they lie alongside one another offering a relatively small profile. Once in position within the surgical site, the arms can be activated into their deployed position in which they diverge.

Preferably, the tissue treatment element is a cutting wire. The cutting wire can conceivably form a loop, or alternatively extend relatively linearly between the arms. As previously mentioned, the cutting wire is disposed at the distal end of each arm such that it is movable between at least two different operating positions. Typically, one of the at least two operating positions is an end effect position, in which the cutting wire extends longitudinally from the end of the arms. Alternatively or additionally, one of the at least two operating positions is a side effect position, in which the cutting wire extends laterally from the arms towards the end thereof. By providing specific end-effect and side-effect configurations, the cutting wire can be moved into an optimum configuration for whichever type of operation is required.

The cutting wire is typically rotatable between its different operating positions, such that the electrode assembly can be switched between its different configurations quickly and easily. Preferably, the electrode assembly includes a wire actuation means for rotating the cutting wire between its different operating positions. The distal ends of the arms are conveniently curved so as to move smoothly over tissue to be treated. Typically, the distal ends of the arms have a circular cross-section. In this way, the arms present a smooth surface capable of riding over the tissue to the treated regardless of which of their operating positions they are in.

Preferably, the arms are pivotably mounted one to the other at a proximal end of each arm. According to one convenient arrangement, the arm actuation means moves the arms by rotating one arm with respect to the other. In this way, the arms rotate from an aligned position to a diverging position. Alternatively, the arm actuation means moves the arms by pushing one arm apart from the other. In this arrangement, the arms deploy by splaying out one from the other. Whichever arrangement is employed, the tissue treatment element is conveniently connected to each arm at the distal end of each arm.

The invention further resides in a method of resecting tissue from within the bladder of a patient, including the steps of:

i) introducing an instrument into the bladder of the patient, the instrument including a cutting wire disposed between two arms, the arms lying alongside one another in a retracted position, ii) deploying the arms into an expanded position in which they diverge one from another, with the cutting wire therebetween, iii) manoeuvring the instrument such that the cutting wire is in contact with tissue to be resected, and iv) moving the instrument laterally with respect the tissue so as to resect tissue from the bladder.

Typically, the method includes the step of supplying electrosurgical cutting energy to the cutting wire, such that the cutting wire constitutes a cutting electrode in a monopolar or bipolar electrode assembly. Preferably, the method includes the additional step of pressing down against the tissue to be resected with the arms, so as to deform a portion of the bladder from a curved shape into a substantially linear surface. One of the problems associated with certain procedures such as bladder resection is that the curved nature of the bladder makes it difficult for the surgeon to determine a clear dissection plane or even the best direction for the dissection to take. This can result in the surgeon dissecting either too much or too little tissue from the bladder. By applying light pressure using the arms of the instrument, a curved tissue surface is straightened out locally between the arms into a linear section, which allows the cutting wire to cut at a constant depth into the tissue. Preferably, this pressing step takes place before moving the instrument laterally, and the pressing is maintained throughout the lateral movement of the instrument.

The invention further resides in a method of surgically removing a bladder tumour comprising the steps of i) introducing an instrument into the bladder of the patient, the instrument including a cutting wire disposed between two arms, the arms lying alongside one another in a retracted position, ii) deploying the arms into an expanded position in which they diverge one from another, with the cutting wire therebetween, iii) manoeuvring the instrument such that the cutting wire is in contact with tissue to be resected, iv) pressing down against the tissue to be resected with the arms, so as to deform a portion of the bladder from a curved shape into a substantially linear surface, v) supplying electrosurgical cutting energy to the cutting wire, and vi) moving the instrument laterally with respect to the tissue while continuing to press down to deform the bladder into a substantially planar surface, so as to resect the tumour and surrounding tissue from the bladder.

BRIEF DESCRIPTION OF THE DRAWINGS

The invention will now be further described, by way of example only, with reference to the accompanying drawings, in which:

FIG. 1 is a perspective view of an electrode assembly in accordance with the present invention, the electrode assembly being shown in a retracted position, FIG. 2 is a perspective view of the electrode assembly of FIG. 1, the electrode assembly being shown in a first deployed position.

DETAILED DESCRIPTION OF EXEMPLARY EMBODIMENTS

Figure 3:
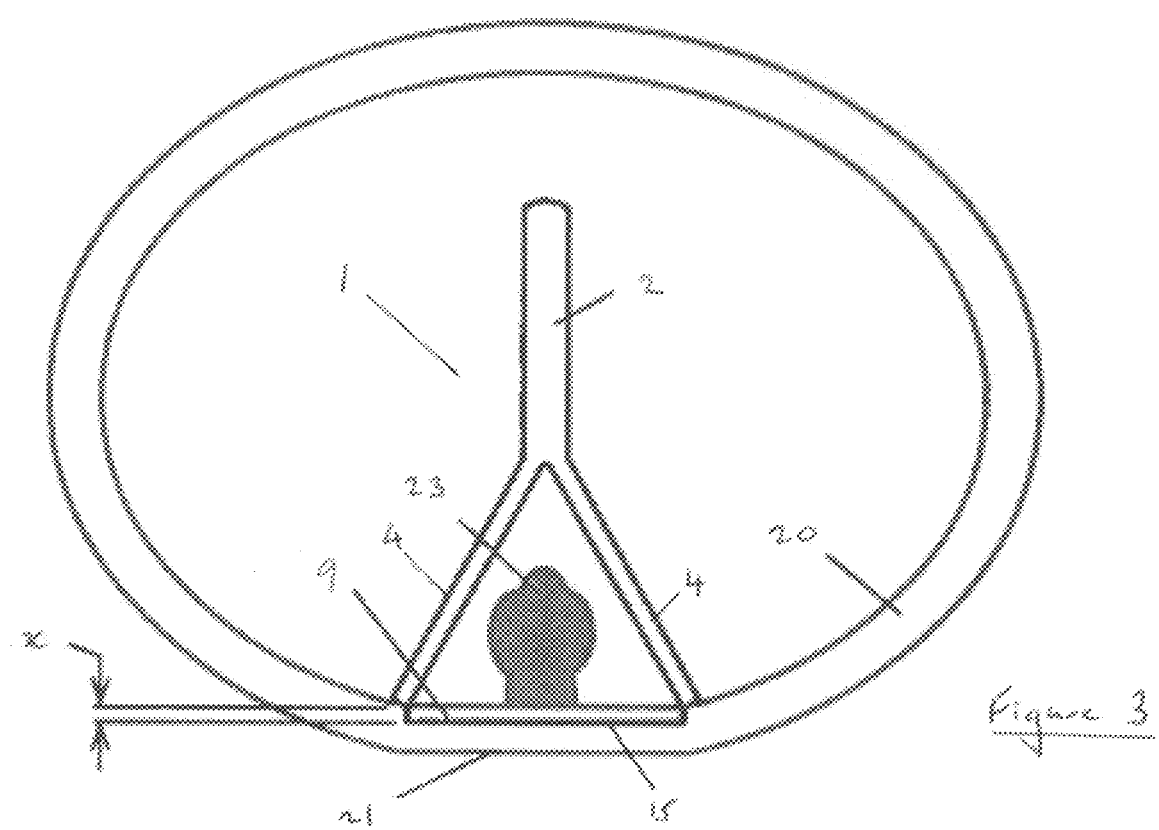
FIG. 3 is a schematic views of the electrode assembly of FIG. 2 being used to resect tissue.

Referring to FIG. 1, an electrosurgical instrument shown generally at 1 includes an elongate shaft 2 and an end effector 3. The end effector 3 comprises first and second arms 4, the arms having a proximal end 5 and a distal end 6. In FIG. 1, the arms 4 lie parallel to one another, but they are pivoted for swivelling movement about pivot pins 7 & 8, the pivot pins being located towards the proximal end 5 of each arm.

An electrosurgical cutting wire electrode 9 interconnects the arms 4 at the distal end 6 of the arms. The wire electrode 9 is mounted on each arm by means of a rotatable mounting, as will be described with reference to FIG. 2. The instrument 1 is introduced using a resectoscope (not shown) into a surgical site such as a human bladder, with the arms in their parallel position as shown in FIG. 1 so as to facilitate insertion of the instrument into the patient.

Once the instrument has been introduced into the surgical site, the end effector is moved to the position shown in FIG. 2. Between the arms 4 is a pushrod 10, attached to two linkages 11 & 12 by means of pivot pins 13 & 14. An actuator (not shown) causes the pushrod 10 to advance, pivoting the linkages 11 & 12 about the pivot pins 13 & 14 into a generally "Y"-shape as shown in FIG. 2. This causes the arms 4 to be splayed apart, such that their distal ends 6 become separated laterally one from another.

The separation of the distal ends of the arms 4 causes the wire electrode 9 to be stretched therebetween. The electrode 9 comprises a relatively flexible central portion 15, which becomes deployed into a substantially straight cutting wire when the arms are splayed apart. The electrode has stiffer portions 16 & 17 adjacent each arm, such that the central portion is offset from the arms by a preset spacing "x". The wire electrode 9 is attached to each arm by means of a rotatable mounting 18, the rotatable mountings in FIG. 2 being oriented such that the central portion 15 of the electrode 9 is offset longitudinally from the arms 4 by the spacing "x".

Figure 4:
FIG. 4 is an additional schematic views of the electrode assembly of FIG. 2 being used to resect tissue.

The use of the instrument 1 will now be described with additional reference to FIGS. 3 & 4. The instrument is shown in proximity to a curved tissue surface, such as a bladder wall 20. The instrument is pressed against the curved bladder wall 20 such that the arms 4 depress the tissue surface 21, causing the tissue therebetween to be straightened into a linear section 22 between the arms. This is the situation shown in FIG. 4. Electrosurgical energy is then supplied to the electrode 9, and the instrument is translated across the tissue surface 21, excising a layer of tissue defined by the preset spacing "x" between the central portion 15 of the electrode and the distal ends of the arms 4. Tissue is removed from the bladder wall 20 along with other target tissue, such as tumour 23.

If a relatively constant downward pressure is applied from the arms 4 onto the tissue surface 21, then the movement of the instrument will cause the removal of a constant depth of tissue, notwithstanding that the tissue surface 21 is naturally curved. Once sufficient tissue has been excised from the bladder wall, the end effector 2 is retracted back into the form shown in FIG. 1, and removed from the surgical site. The excised tissue can be removed from the surgical site separately, for example using a surgical graspers and a tissue bag (not shown).

Figure 5:
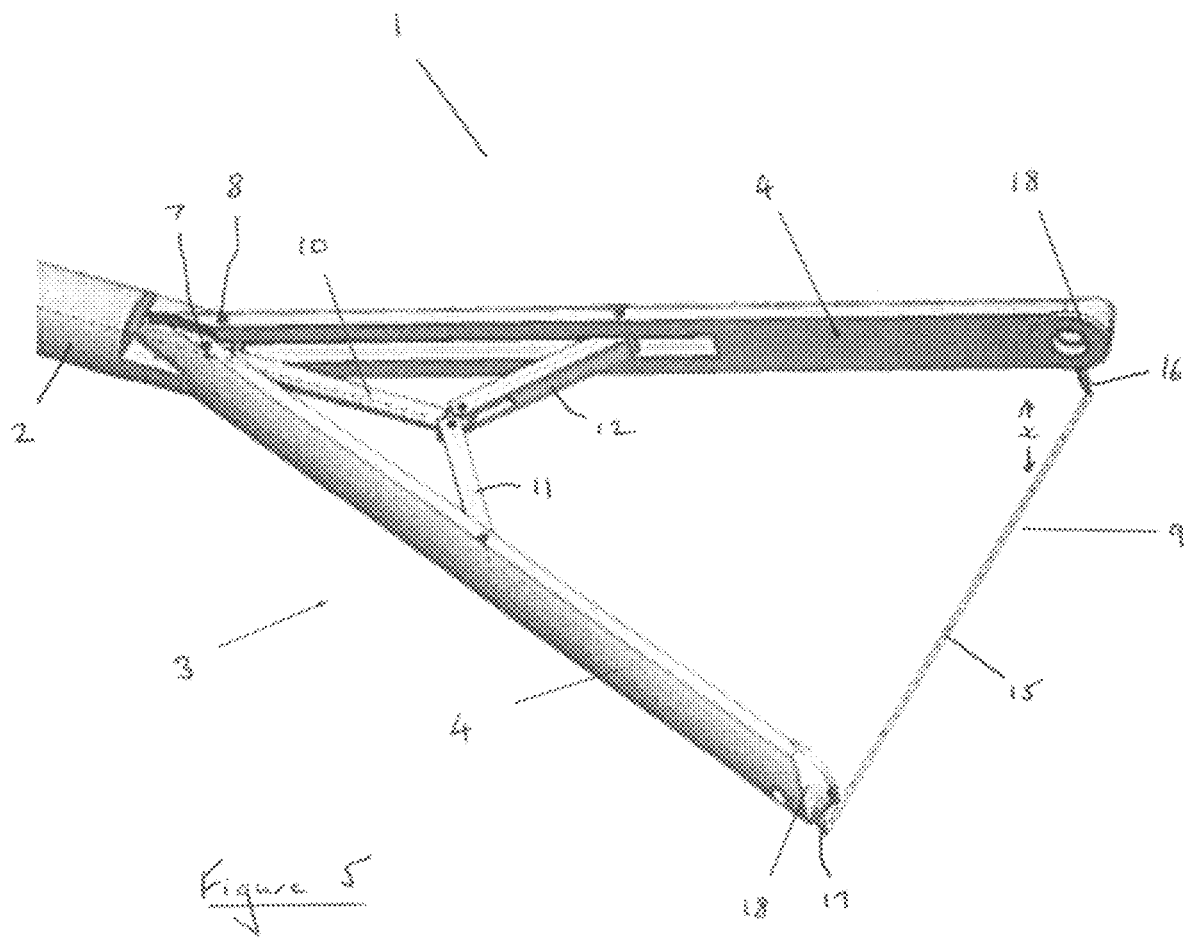
FIG. 5 is a perspective view of the electrode assembly of FIG. 1, the electrode assembly being shown in a second deployed position.

The end effector of FIG. 2 acts as an end-effect instrument, with the central portion 15 of the electrode 9 being offset longitudinally from the arms 4. FIG. 5 shows the instrument 1 in a configuration to act as a side-effect instrument. In this instance, the rotatable mountings 18 have been rotated such that the electrode protrudes laterally from the arms 4, with the central portion 15 extending laterally from the end of the arms by the preset offset "x". An actuator (not shown) may be present to rotate the mountings 18 between the positions shown in FIGS. 2 & 5.

The operation of the instrument of FIG. 5 is substantially as before, with pressure being applied by the arms 4 to the tissue to be treated. However, with the electrode 9 in the side-effect position of FIG. 5, the instrument is pressed laterally against the tissue, and then translated parallel to the surface of the tissue, usually in a retrograde manner. As before, once sufficient tissue has been excised from the bladder wall, the end effector 3 is retracted back into the form shown in FIG. 1, and removed from the surgical site.

Those skilled in the art will appreciate that arrangements other than those described above can be employed without departing from the scope of the present invention. For example, while the embodiments of FIGS. 1 to 5 illustrate the use of a wire electrode, other electrodes such as rollers, sliders or buttons can be employed, with the arms 4 still being deployed between parallel and splayed positions. Where a wire electrode is employed, various wire cross-sections may be envisaged, ranging from generally circular cross-sections for simple cutting to various flatter or other shaped cross-sections capable of providing an element of haemostasis along with the cutting action. The wire electrode may also be distended in different ways, either linearly as shown in FIGS. 2 & 5, or with a more curved profile. Whichever form of electrode is employed, the arms can be used to press against tissue to form a linear resection plane, and ensuring that a predetermined distance "x" is maintained between the arms and the cutting surface of the electrode, whatever type of electrode is employed.

What is claimed is:

1. A method of resecting tissue from within a bladder of a patient, including steps of
   i) introducing an instrument into the bladder of the patient, the instrument including a cutting wire disposed between two arms, the two arms lying alongside one another in a retracted position,
   ii) deploying the two arms into an expanded position in which the two arms diverge one from another, with the cutting wire therebetween,
   iii) rotating the cutting wire about an axis running between a distal end of the two arms such that the cutting wire is displaced from its original position by a preset offset spacing,
   iv) maneuvering the instrument such that the cutting wire is in contact with tissue to be resected, and
   v) moving the instrument laterally with respect to the tissue so as to resect tissue from the bladder.

2. A method according to claim 1 including a step of supplying electrosurgical cutting energy to the cutting wire.

3. A method according to claim 1, including an additional step of pressing down against the tissue to be resected with the two arms, so as to deform a portion of the bladder from a curved shape into a substantially linear surface.

4. A method according to claim 3, wherein the pressing step takes place before moving the instrument laterally, and the pressing is maintained throughout the lateral movement of the instrument.

5. A method of surgically removing a bladder tumour comprising steps of
   i) introducing an instrument into a bladder of a patient, the instrument including a cutting wire disposed between two arms, the two arms lying alongside one another in a retracted position,
   ii) deploying the two arms into an expanded position in which the two arms diverge one from another, with the cutting wire therebetween,
   iii) rotating the cutting wire about an axis running between a distal end of the two arms such that the cutting wire is displaced from its original position by a preset offset spacing,
   iv) maneuvering the instrument such that the cutting wire is in contact with tissue to be resected,
   v) pressing down against the tissue to be resected with the two arms, so as to deform a portion of the bladder from a curved shape into a substantially linear surface,
   vi) supplying electrosurgical cutting energy to the cutting wire, and
   vii) moving the instrument laterally with respect the tissue while continuing to press down to deform the bladder into a substantially planar surface, so as to resect the bladder tumour and surrounding tissue from the bladder.

* * * * *